United States Patent [19]

Calvino et al.

[11] Patent Number: 4,671,818
[45] Date of Patent: Jun. 9, 1987

[54] COMPOSITIONS CONTAINING HETEROCYCLIC COMPOUNDS AND THEIR USE AS HERBICIDES

[75] Inventors: Rosella Calvino, Turin; Roberta Fruttero, Savigliano; Vittorio Messori; Francesco Rodio, both of Turin, all of Italy

[73] Assignee: Enichem Sintesi S.P.A., Plaermo, Italy

[21] Appl. No.: 770,482

[22] Filed: Aug. 29, 1985

[30] Foreign Application Priority Data

Aug. 29, 1984 [IT] Italy ............... 22449 A/84

[51] Int. Cl.$^4$ ........................... A01N 43/82
[52] U.S. Cl. ........................... 71/92; 71/88; 71/90
[58] Field of Search ........................... 71/92

[56] References Cited

U.S. PATENT DOCUMENTS 3,937,715 2/1976 Rochling et al. ............ 71/92
4,502,881 3/1985 Francese et al. ............ 71/92

FOREIGN PATENT DOCUMENTS 6800779 1/1968 South Africa ............ 548/125
0502365 3/1971 Switzerland ............ 548/125
0508650 7/1971 Switzerland ............ 548/125

OTHER PUBLICATIONS

Fundaro, "Action of Some Furazans, etc.", (1974), ca 83:108147f, (1975).
Calvino et al, "Synthesis and Preliminary, etc.", (1977), ca 88:50742f, (1978).
Westphal et al, "3-Amino-1,2,5-oxadiazoles", (1973), ca 79:105152k, (1973).
Gasco et al, "Chemistry of 1,2,5-oxadiazoles", (1971), ca 75:35888w, (1971).

Primary Examiner—Glennon H. Hollrah
Assistant Examiner—A. Owens
Attorney, Agent, or Firm—Sughrue, Mion, Zinn, Macpeak & Seas

[57] ABSTRACT

Compositions containing heterocyclic compounds are described which include an amide group, can act as herbicides and be defined by the general formula:

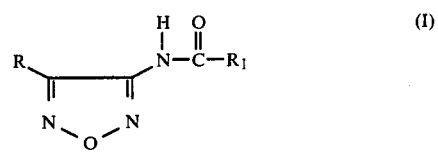

in which:
R is a linear or branched alkyl group containing from 1 to 6 carbon atoms;
 the phenyl group;
 a phenyl group having a substituent, or several substituents which may be identical or different from each other, selected from the halogens and alkyl ($C_1$-$C_4$), oxyalkyl ($C_1$-$C_4$), halogenoalkyl ($C_1$-$C_4$) and nitro groups;
$R_1$ is a linear or branched alkyl group containing from 1 to 12 carbon atoms;
 a linear or branched alkyl group containing from 1 to 12 carbon atoms substituted with one or more halogen atoms;
 a cycloalkyl group containing from 3 to 8 carbon atoms;
 a (methyleneoxy)alkyl ($C_1$-$C_5$) group;
 a (methyleneoxy)phenyl group;
 a (methyleneoxy)phenyl group having one or more substituents in the ring which are selected from halogen, ($C_1$-$C_4$) alkyl, ($C_1$-$C_4$) halogenoalkyl groups;
 the phenyl group;
 the benzyl group;
 a phenyl or benzyl group having one or more substituents, which may be identical or different from each other, selected from halogen atoms and ($C_1$-$C_4$) alkyl, ($C_1$-$C_4$) halogenalkyl, ($C_1$-$C_4$) oxyalkyl and nitro groups;
or $R_1$ is definable by:

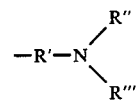

where R' is a ($C_1$-$C_2$) alkylene group and R" and R''' are linear or branched alkyl groups containing from 1 to 5 carbon atoms; or R" and R''' taken together with the nitrogen atom to which they are connected form a 5 or 6 membered heterocyclic ring possibly containing another heteroatom selected from O, N and S.

5 Claims, No Drawings

COMPOSITIONS CONTAINING HETEROCYCLIC COMPOUNDS AND THEIR USE AS HERBICIDES

BACKGROUND OF THE INVENTION

The present invention relates to compositions containing heterocyclic compounds having an amide function and having herbicidal activities, to their use in the control and destruction of infestant plants and to the process for preparing them.

It is known that there is a great need in agricolture for new, alternative herbicidal products which have high activities in the elimination of weeds together with a substantial lack of toxicity to man and animals.

According to the present invention these requirements are satisfied by means of new herbicidal compounds having a heterocyclic structure and having an amide group attached to the hetrocyclic structure.

Accordingly the present invention relates to a method for controlling the growth of infestant plants, characterised in that the infested ground is treated with an effective quantity of a herbicidal compound or of a composition containing a herbicidal compound, selected from those which can be defined by the general formula:

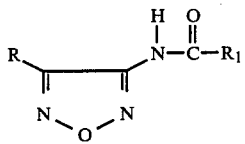

in which:
R is a linear or branched alkyl group containing from 1 to 6 carbon atoms;
  the phenyl group;
  a phenyl group having a substituent, or several substituents which may be identical or different from each other, selected from the halogens and alkyl ($C_1$–$C_4$), oxyalkyl ($C_1$–$C_4$), halogenoalkyl ($C_1$–$C_4$) and nitro groups;
$R_1$ is a linear or branched alkyl group containing from 1 to 12 carbon atoms;
  a linear or branched alkyl group containing from 1 to 12 carbon atoms substituted with one or more halogen atoms;
  a cycloalkyl group containing from 3 to 8 carbon atoms;
  a (methyleneoxy)alkyl ($C_1$–$C_5$) group;
  a (methyleneoxy)phenyl group;
  a (methyleneoxy)phenyl group having one or more substituents in the ring which are selected from halogen, ($C_1$–$C_4$) alkyl, ($C_1$–$C_4$) halogenoalkyl groups;
  the phenyl group;
  the benzyl group;
  a phenyl or benzyl group having one or more substituents, which may be identical or different from each other, selected from halogen atoms and ($C_1$–$C_4$) alkyl, ($C_1$–$C_4$) halogenalkyl, ($C_1$–$C_4$) oxyalkyl and nitro groups;
or $R_1$ is definable by:

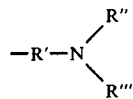

where R' is a ($C_1$–$C_2$) alkylene group and R" and R''' are linear or branched alkyl groups containing from 1 to 5 carbon atoms; or R" and R''' taken together with the nitrogen atom to which they are connected form a 5 or 6 membered heterocyclic ring possibly containing another heteroatom selected from O, N and S.

In the definitions above, halogen is intended to mean fluorine, chlorine, bromine or iodine.

Examples of preferred substituents in the general formula (I) given above are:
R=methyl
$R_1$=methyl, isopropyl, isobutyl, chloromethyl, cyclobutyl, cyclohexyl, phenyl, chlorophenyl, dichlorophenyl, bromophenyl, fluorophenyl, nitrophenyl, t-butylphenyl and trifluoromethylphenyl.

Specific examples of compounds which fall within the general formula (I) above are:
N-(4-methylfurazan-3-yl)cyclopropanecarboxamide;
N-(4-methylfurazan-3-yl)methylcarboxamide;
N-(4-methylfurazan-3-yl)isopropylcarboxamide;
N-(4-methylfurazan-3-yl)isobutylcarboxamide;
N-(4-methylfurazan-3-yl)benzylcarboxamide;
N-(4-methylfurazan-3-yl)chloromethylcarboxamide;
N-(4-methylfurazan-3-yl)cyclohexanecarboxamide;
N-(4-methylfurazan-3-yl)-2-methylphenylcarboxamide;
N-(4-methylfurazan-3-yl)-4-methylphenylcarboxamide;
N-(4-methylfurazan-3-yl)-4-chlorophenylcarboxamide;
N-(4-methylfurazan-3-yl)-2,4-dichlorophenylcarboxamide;
N-(4-methylfurazan-3-yl)-2-idodophenylcarboxamide;
N-(4-methylfurazan-3-yl)-3-fluorophenylcarboxamide;
N-(4-methylfurazan-3-yl)-3,4-dichlorophenylcarboxamide;
N-(4-methylfurazan-3-yl)-4-tert-butylphenylcarboxamide;
N-(4-methylfurazan-3-yl)-3-trifluoromethylphenylcarboxamide;
N-(4-methylfurazan-3-yl)-2-bromophenylcarboxamide;
N-(4-methylfurazan-3-yl)cyclobutanecarboxamide;
N-(4-methylfurazan-3-yl)-4-nitrophenylcarboxamide;
N-(4-methylfurazan-3-yl)phenylcarboxamide;
N-(4-methylfurazan-3-yl)methylene-oxy-2,4-dichlorophenylcarboxamide.

Some of the compounds represented by the general formula (I) such as those in which R is the methyl group and $R_1$ is methyl or N-diethyl-methylene-amine or N-methylene-morpholine are known from the literature which describes their synthesis, their physical and chemical characteristics and, in some cases, their pharmacological properties. In this respect one is referred to the following literature:
Il farmaco, Ed Sci. 26, 233 (1971);
Il farmaco, Ed Sci. 32, 789 (1977);
J. Prakt. Chem. 315, 791 (1973);
Swiss Pat. No. 502.365; and
Swisse Pat. No. 508.650.

The present invention is based on the discovery that these known compounds and other new compounds falling within the general formula (I) have herbicidal activities with a wide spectrum of action against infestant plants, but are substantially innocuous to man and animals.

The compounds (I) may be synthesised by the following reaction scheme.

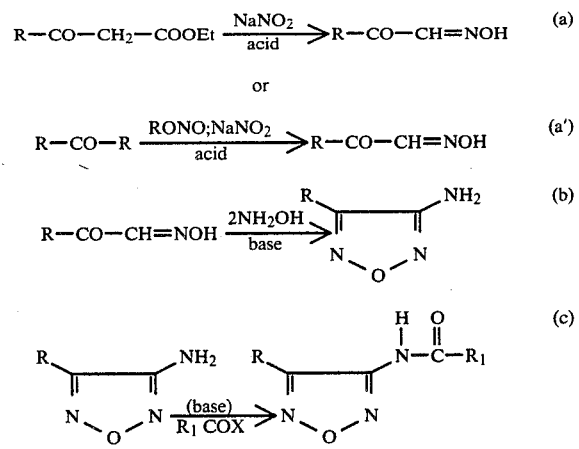

In the formulae above, R and $R_1$ have the meaning indicated previously and X represents a halogen, preferably chlorine.

Typically the basic step of the process of the present invention for preparing the compounds having the general formula (I) is consisting of reacting a 3-amine-(4-R-substituted)-furazan (II) with an acyl chloride $R_1$COCl (III), wherein R and $R_1$ have the same meaning of the general formula (I), with a (III) to (II) molar ratio of from 1:1 to 1.2:1, at a temperature of from 0° to 100° C., in the presence of a basic compound blocking the halogenic acid, in an inert organic solvent, for a time of from 1 to 10 hours and of recovering the compound (I) from the reaction mixture by filtration. The preferred solvent for the reaction is ethyl ether and the preferred basic compound blocking the halogenic acid is pyridine.

The compounds (I) according to the present invention have good herbicidal activities particularly when used under post-emergence conditions in doses of from 0.1 Kg/hectare up to a maximum of 5 Kg/hectare. Moreover, the herbicidal activity of the compounds (I) is highly selective with regard to crops belonging to the grass family (gramineae) up to doses of 2-2.5 Kg/hectare; at higher doses the herbicidal activity of the compounds tends to become total.

The compounds (I) of the present invention are herbicides which interfere both whith the seed germination phase and with the subsequent development of the embryo plants. They have good herbicidal activities and may thus be used conveniently in post-emergence weed killing in crops, in accordance with the different degrees of selectivity shown and the biological cycles of the infestants.

The compounds (I) of the present invention may be applied by the usual methods, in solution, suspension or emulsion, as powders or as granules, according to the chosen application, as long as the active principle is finely divided.

The compositions of the present invention are typically prepared by the mixture of the active ingredient with an adjuvant including diluents, fillers, extenders and conditioning agents to provide the compositions in the form of finely-divided solid particles, granules, solutions, dispersions or emulsions. The active ingredient may thus be used with an adjuvant such as a finely-divided solid, an organic liquid, water, a wetting agent, a dispersing agent or any suitable combination thereof. The herbicidal compositions of the present invention, particularly liquids or soluble powders, preferably contain one or more surface active agents as conditioning agents in quantities sufficient to render a particular composition readily dispersible in water in oil. The incorporation of a surface active agent in the composition greatly improves its effectiveness. By "surface active agents" are meant wetting agents, dispersing agents, suspensing agents, and emulsifying agents. Anionic, cationic or non-ionic agents may be used equally well.

Preferred wetting agents are alkylbenzene sulphonates, alkylnaphthalene sulphonates, aliphatic alcohol sulphonates, polyoxyethylene derivative of alkylphenols (particularly isooctylphenol and nonylphenol)

Compositions of powders dispersible in water may be made with one or more active ingredients, an inert solid filler and one or more wetting and dispersing agents. The solid inert fillers are usually of mineral origin, for example natural clays, diatomaceous earths and synthetic minerals derived from silica and the like. Examples of such fillers comprise kaolin, attapulgite and synthetic magnesium silicate. The powders of the present invention which are dispersible in water usually contain about 5 to about 95 parts by weight of the active ingredient, from about 0.25 to about 25 parts by weight of the wetting agent, from about 0.25 to about 25 parts by weight of the dispersing agent and from about 4.5 to about 94.5 parts by weight of the solid inert filler, all the parts being with reference to the total weight of the composition.

The aqueous suspensions may be prepared by mixing and grinding together an aqueous suspension of the active ingredient which is insoluble in water to obtain a concentrated suspension of very finely divided particles. The resulting concentrated aqueous suspension has extremely small particles such that when it is diluted and sprayed the coating is very uniform.

The emulsifiable oils are generally solutions of the active ingredient in solvents which are immiscible or slightly miscible with water, together with a surface active agent. Solvents suitable for the active ingredients of the present invention include hydrocarbons and ethers, esters and ketones which are immiscible with water. The composition of the emulsifiable oil generally contains from about 5 to about 95 parts by weight of the active ingredient, from about 1 to about 50 parts by weight of surfactant and from about 4 to about 94 parts by weight of solvent, all the parts being based on the total weight of the emulsifiable oil.

The experimental examples which follow are given by way of example and are non-limitative of the invention.

EXAMPLE 1

Synthesis of N-(4-methylfurazan-3-yl)cyclopropanecarboxamide 4-methyl-3-aminofurazan is first prepared from isonitrosoacetone by the general method described in Berichte 13, 1328 (1882), followed by cyclization as described in Gazz.Chim.Ital.81,106 (1951).

5 g (about 0.05 moles) of 4-methyl-3-aminofurazan, 50 ml of ethyl ether and 4 ml of pyridine are then loaded into a 100 ml glass reactor. This is cooled to a temperature of from 0° to 10° C. and 5 ml (0.06 moles) of the chloride of cyclopropanecarboxylic acid are added under agitation. Heating is then carried out under reflux for about one hour. After cooling of the reaction mass, the ether is evaporated and the residual solid is transferred into about 100 ml of water. Slight heating is effected for about 30 minutes and then the mass is cooled and filtered, the solid being washed with water. The solid obtained is dried in an oven at 90° C.

The compound in the title is obtained with a yield of 80% with respect to the theoretical value in the form of a white crystalline solid with a melting point of 166°–167° C., crystallised from diisopropyl ether. The structure of the compound is confirmed by routine spectroscopy (IR, NMR), mass spectrometry and elementary analysis (values within a range of ±0.3% of the theoretical).

The reactions being carried out along the general lines of example 1, with the chloride of the suitable acid being substituted for the chloride of cyclopropanecarboxylic acid, the compounds of the following examples were obtained in which the substituents R and $R_1$ are defined by the general formula (I).

EXAMPLES 2 TO 18

|  |  | Melting point (°C.) (solvent of crystallization) |
|---|---|---|
| Example 2 | R = methyl<br>$R_1$ = methyl | 115–116° C.<br>(diisopropyl ether) |
| Example 3 | R = methyl<br>$R_1$ = isopropyl | 131–132° C.<br>(diisopropyl ether) |
| Example 4 | R = methyl<br>$R_1$ = isobutyl | 105–106° C.<br>(cyclohexane) |
| Example 5 | R = methyl<br>$R_1$ = benzyl | 151–152° C.<br>(diisopropyl ether) |
| Example 6 | R = methyl<br>$R_1$ = cyclohexyl | 151° C.<br>(cyclohexane) |
| Example 7 | R = methyl<br>$R_1$ = 2-methylphenyl | 123–124° C.<br>(diisopropyl ether) |
| Example 8 | R = methyl<br>$R_1$ = 4-methylphenyl | 143–144° C.<br>(diisopropyl ether) |
| Example 9 | R = methyl<br>$R_1$ = 4-chlorophenyl | 171–172° C.<br>(chloroform) |
| Example 10 | R = methyl<br>$R_1$ = 2,4-dichlorophenyl | — |
| Example 11 | R = methyl<br>$R_1$ = 3-fluorophenyl | 124–125° C.<br>(cyclohexane) |
| Example 12 | R = methyl<br>$R_1$ = 3,4-dichlorophenyl | — |
| Example 13 | R = methyl<br>$R_1$ = 4-tert-butylphenyl | — |
| Example 14 | R = methyl<br>$R_1$ = 3-trifluoromethylphenyl | — |
| Example 15 | R = methyl<br>$R_1$ = 2-bromophenyl | — |
| Example 16 | R = methyl<br>$R_1$ = cyclobutyl | 134–135° C.<br>(diisopropyl ether) |
| Example 17 | R = methyl<br>$R_1$ = phenyl | — |
| Example 18 | R = methyl<br>$R_1$ = methylene-oxy-2,4-dichlorophenyl | — |

Evaluation of the herbicidal activity

All the plants were cultivated in greenhouses in sterilised, fertilized ground at a controlled temperature (20±5° C.) and with a relative humidity of 60±10%. All the species were also cultivated in plastic containers having a size of 22×15×6 cm. The compounds described in the above examples were formulated as wettable powders, suspensions or water-acetone solutions with 10% of the active principle.

Post-emergence test

The plants were treated when they had reached the stage of 2–3 leaves, about 14 days after seeding.

The post-emergence treatment was carried out with the use of an Oxford precision pump at pressures of 5 psi (0.35 bar).

The evaluation was carried out ten days after the treatment. The effect of the active principle was evaluated according to a scale of from 0 to 4 in which:

0 = no damage;
1 = 25% damage;
2 = 50% damage;
3 = 75% damage;
4 = 100% damage.

The results of the tests are given in tables 1 and 2 below.

TABLE 1

Post-emergence treatment with active principle doses of 2 kg/hectare

|  | Ex. 1 | Ex. 4 | Ex. 6 | Ex. 7 | Ex. 8 | Ex. 9 | Ex. 10 | Ex. 13 | Ex. 17 |
|---|---|---|---|---|---|---|---|---|---|
| Crop | | | | | | | | | |
| Soybean | 4 | 4 | 4 | 4 | 4 | 4 | 4 | 4 | 3 |
| Rice | 0 | 1 | 2 | 1 | 1 | 1 | 0 | 1 | 1 |
| Maize | 2 | 2 | 2 | 2 | 1 | 1 | 1 | 2 | 1 |
| Oats | 2 | 2 | 2 | 2 | 1 | 1 | 2 | 2 | 1 |
| Wheat | 1 | 1 | 2 | 1 | 1 | 1 | 1 | 1 | 1 |
| Beet | 2 | 4 | 4 | 4 | 4 | 4 | 4 | 4 | 3 |
| Infestants | | | | | | | | | |
| Stellaria (Chickweed) | 4 | 4 | 4 | 4 | 4 | 4 | 4 | 4 | 4 |
| Veronica | 2 | 1 | 2 | 1 | 1 | 1 | 2 | 1 | 1 |
| Chenopodium (Goosefoot) | 3 | 3 | 4 | 4 | 3 | 4 | 4 | 3 | 4 |
| Digitaria (Crabgrass) | 2 | 1 | 4 | 2 | 1 | 4 | 2 | 1 | 2 |
| Setaria | 3 | 1 | 4 | 2 | 2 | 3 | 3 | 3 | 2 |
| Alopecurus | 3 | 2 | 3 | 2 | 2 | 2 | 2 | 2 | 1 |

TABLE 2

Post-emergence treatment with doses of 5 kg/hectare

| Species | Ex. 1 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|---|---|---|---|---|---|---|---|
| BETA V. | 3 | 2 | 4 | 2 | 4 | 4 | 4 | 4 | 4 | 3 | 3 | 4 | 1 | 4 | 3 | 4 | 4 |
| PISUM S. | 4 | 2 | 4 | 2 | 4 | 4 | 2 | 4 | 4 | 2 | 2 | 4 | 3 | 4 | 4 | 4 | 4 |

TABLE 2-continued

| | Post-emergence treatment with doses of 5 kg/hectare | | | | | | | | | | | | | | | | |
|---|---|---|---|---|---|---|---|---|---|---|---|---|---|---|---|---|---|
| Species | Ex. 1 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 | Ex. 17 | Ex. 18 |
| SOLANUM L. | 3 | 2 | 4 | 4 | 4 | 4 | 4 | 4 | 4 | 4 | 3 | 4 | 1 | 4 | 1 | 4 | 4 |
| CICHORIUM I. | 2 | 1 | 4 | 3 | 4 | 4 | 4 | 4 | 4 | 3 | 2 | 4 | 1 | 4 | 4 | 4 | 4 |
| LINUM U. | 4 | 3 | 4 | 4 | 4 | 4 | 4 | 4 | 4 | 4 | 3 | 4 | 1 | 4 | 4 | 4 | 4 |
| ZEA MAYS | 1 | 0 | 2 | 2 | 2 | 2 | 1 | 1 | 2 | 2 | 2 | 2 | 0 | 2 | 2 | 1 | 1 |
| LOLIUM I. | 1 | 0 | 2 | 1 | 2 | 2 | 1 | 1 | 2 | 1 | 1 | 2 | 0 | 2 | 2 | 1 | 1 |
| AVENA S. | 1 | 0 | 2 | 2 | 2 | 2 | 1 | 1 | 2 | 2 | 2 | 2 | 0 | 2 | 2 | 1 | 2 |

Examples of the preparation of compositions containing the herbicidal compounds of the present invention are given below.

Preparation of concentrates that can be emulsified

Ten parts by weight of active principle are dissolved in 80 parts by weight of a mixture of cyclohexanone and xylene (50/50 by volume) under slow, continuous agitation, at a temperature of from ambient (20°-25° C.) to about 50° C. The mixture is left under agitation until the whole of the solid has dissolved. The solution obtained is filtered through a sintered silica plate filter to remove any insoluble residue and then ten parts by weight of emulsifying agent constituted by a mixture (1:1 by weight) of ionic surfactant and non-ionic surfactant is added at ambient temperature with agitation. The ionic surfactant is constituted by the calcium salt of dodecyl-benzene sulphonic acid. The non-ionic surfactant is constituted by ether/ether of palmitic or oleic acid condensed with 18-15 moles of ethylene oxide.

Preparation of wettable powders

To ten parts by weight of ground active principle are added 80 parts by weight of a mixture of inert substances constituted by 60 parts by weight of kaolin, 15 parts by weight of diatomaceous earth and 5 parts by weight of colloidal silica. The mixture obtained is thoroughly homogenised in a ball mill, agitation being maintained for 2 hours. The product obtained is ground to a grain size of less than 40 microns by grinding in a blade mill, a composition thus being obtained which is suitable for dispersion in water.

Preparation of concentrated suspensions

The active principle is dispersed in a base liquid containing a surfactant. More particularly, 40 parts by weight of active principle in the form of a very fine powder, such as that obtained by grinding in a pin mill or micronization in an air jet mill, are mixed slowly in a homogenizer with the base liquid constituted by 45 parts by weight of demineralised water, 5 parts by weight of ethylene glycol and 5 parts by weight of surfactant. The latter is a calcium salt of dodecylbenzene sulphonic acid mixed with polyoxyethylene monosterarate.

A paste is thus obtained which may be further refined by passage through a ball mill.

We claim:

1. A method for controlling infestant weeds comprising applying a herbicidally effective amount of a herbicidal composition including from 5 to 95% by weight of a compound having the general formula:

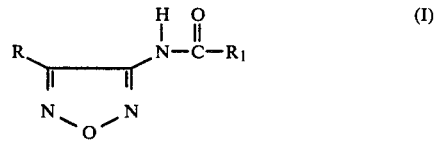

in which:

R is methyl; and $R_1$ is a linear or branched alkyl group containing from 1 to 4 carbon atoms, phenyl, methylene-oxy-2,4-dichlorophenyl, cycloalkyl containing from 3 to 6 carbon atoms or phenyl substituted with one or two atoms of Fl, Cl or Br, or phenyl substituted with an alkyl radical containing from 1 to 4 carbon atoms or substituted with trifluoromethyl; and 1 or more inert adjuvants including diluents, wetting agents, dispersants and solvents to a locus to be protected.

2. Method according to claim 1, characterised in that $R_1$ is methyl, isopropyl, isobutyl, cyclobutyl, cyclohexyl, phenyl, chlorophenyl, dichlorophenyl, bromophenyl, fluorophenyl, t-butylphenyl or trifluoromethylphenyl.

3. Method according to claim 1, characterised in that the ground is treated with from 0.1 to 5 kg/hectare of herbicidal compound.

4. Method according to claim 1, characterised in that the treatment is carried out after emergence.

5. A method for controlling infestant weeds comprising applying to a locus to be treated a herbicidally effective amount of a compound having the general formula:

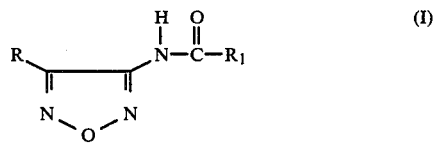

in which:

R is methyl; and $R_1$ is a linear or branched alkyl group containing from 1 to 4 carbon atoms, phenyl, methylene-oxy-2,4-dichlorophenyl, cycloalkyl containing from 3 to 6 carbon atoms or phenyl substituted with one or two atoms of Fl, Cl or Br, or phenyl substituted with an alkyl radical containing from 1 to 4 carbon atoms or substituted with trifluoromethyl.

* * * * *